United States Patent
Martínez de Castaneda et al.

(10) Patent No.: US 10,401,270 B2
(45) Date of Patent: Sep. 3, 2019

(54) METHOD OF DESIGN AND MANUFACTURING CONCRETE STRUCTURES BASED ON THE VERIFICATION OF CONCRETE FATIGUE STRENGTH BY TEST

(71) Applicant: PACADAR, SA, Madrid (ES)

(72) Inventors: Francisco Javier Martínez de Castaneda, Madrid (ES); Juan Carlos Lancha Fernández, Illescas Toledo (ES); Manuel Cidoncha Escobar, Madrid (ES); María Celia Gómez del Pulgar González, Ciudad Real (ES)

(73) Assignee: PACADAR, SA, Madrid (ES)

( * ) Notice: Subject to any disclaimer, the term of this patent is extended or adjusted under 35 U.S.C. 154(b) by 0 days.

(21) Appl. No.: 15/773,313

(22) PCT Filed: Jun. 7, 2017

(86) PCT No.: PCT/IB2017/053351
§ 371 (c)(1),
(2) Date: May 3, 2018

(87) PCT Pub. No.: WO2017/212411
PCT Pub. Date: Dec. 14, 2014

(65) Prior Publication Data
US 2018/0372604 A1    Dec. 27, 2018

(30) Foreign Application Priority Data
Jun. 8, 2016  (EP) .................................... 16001287

(51) Int. Cl.
*G01N 3/32* (2006.01)
*E02D 33/00* (2006.01)
(Continued)

(52) U.S. Cl.
CPC .......... *G01N 3/32* (2013.01); *B28B 17/0081* (2013.01); *E02B 1/00* (2013.01); *E02B 3/06* (2013.01);
(Continued)

(58) Field of Classification Search
CPC .... G01N 3/32; G01N 33/383; B28B 17/0081; E02B 1/00; E02B 3/06; E02B 17/00;
(Continued)

(56) References Cited

U.S. PATENT DOCUMENTS

2012/0070233 A1* 3/2012 Wang ..................... E02D 27/42
405/232
2014/0245671 A1  9/2014 Sritharan et al.
2015/0337517 A1* 11/2015 Hall ........................ E02B 17/02
405/227

FOREIGN PATENT DOCUMENTS

CN  102466586  5/2012

OTHER PUBLICATIONS

European Search Report issued for priority application No. 16001287.8 dated Feb. 17, 2017.
(Continued)

*Primary Examiner* — David Z Huang
(74) *Attorney, Agent, or Firm* — Silvia Salvadori (57) ABSTRACT

Method of design and manufacturing concrete structures subjected to relevant cyclic loads along their service lives, as wind towers, and a fatigue testing machine. The method consists on the design of concrete structures conditioned by cyclic loads considering a fatigue strength value specified by the project as one of the main design parameters, which will be verified during the manufacturing phase as one of the control parameters of the quality assurance plan by performing fatigue strength test on concrete samples representative of the concrete structural elements produced on said manu- (Continued)

facturing phase. The method allows to decouple the concrete fatigue strength from the compressive strength of the material, which is why includes a verification of the fatigue strength as a part of a quality assurance plan of production according to a new developed procedure.

13 Claims, 6 Drawing Sheets

(51) Int. Cl.
　　*G05B 19/418*　　(2006.01)
　　*E02D 27/42*　　(2006.01)
　　*G01N 33/38*　　(2006.01)
　　*B28B 17/00*　　(2006.01)
　　*E02B 1/00*　　(2006.01)
　　*E02B 3/06*　　(2006.01)
　　*E02B 17/00*　　(2006.01)
　　*F16M 5/00*　　(2006.01)
　　*E01B 1/00*　　(2006.01)
　　*E01B 3/28*　　(2006.01)
　　*E01D 19/12*　　(2006.01)
　　*E04B 1/06*　　(2006.01)
　　*E04C 5/08*　　(2006.01)
　　*E04H 12/12*　　(2006.01)

(52) U.S. Cl.
　　CPC ............ *E02B 17/00* (2013.01); *E02D 27/425* (2013.01); *E02D 33/00* (2013.01); *F16M 5/00* (2013.01); *G01N 33/383* (2013.01); *G05B 19/41875* (2013.01); *E01B 1/002* (2013.01); *E01B 3/28* (2013.01); *E01B 2204/09* (2013.01); *E01D 19/125* (2013.01); *E02B 2017/0091* (2013.01); *E02D 2250/0023* (2013.01); *E02D 2300/002* (2013.01); *E02D 2300/0051* (2013.01); *E02D 2300/0064* (2013.01); *E04B 1/06* (2013.01); *E04B 2103/02* (2013.01); *E04C 5/08* (2013.01); *E04H 12/12* (2013.01); *G01N 2203/0073* (2013.01); *G05B 2219/32183* (2013.01); *Y02P 90/20* (2015.11); *Y02P 90/22* (2015.11); *Y02P 90/265* (2015.11)

(58) Field of Classification Search
　　CPC ........ E02D 27/425; E02D 33/00; F16M 5/00; G05B 19/41875
　　See application file for complete search history.

(56) References Cited

OTHER PUBLICATIONS

Guideline for the Certification of Wind Turbines Edition 2010, Jul. 1, 2010, pp. 1-389 XP055133625 retrieved from internet.
International Search Report and Written Opinion issued for International patent application No. PCT/IB2017/053351 dated Oct. 23, 2017.

* cited by examiner

METHOD OF DESIGN AND MANUFACTURING CONCRETE STRUCTURES BASED ON THE VERIFICATION OF CONCRETE FATIGUE STRENGTH BY TEST

RELATED APPLICATIONS

This application is a US national phase application of international application number PCT/I62017/053351, filed 7 Jun. 2017, which designates the US and claims priority to European application EP16001287.8 filed 8 Jun. 2016, the contents of each of which are hereby incorporated by reference as if set forth in their entireties.

The present invention generally relates to a structural design method based on the verification of concrete fatigue strength by tests, as main control parameter of the quality assurance plan of a precast concrete production chain.

TECHNICAL FIELD

The invention relates to materials science and civil engineering, and in particular to the design of concrete structures exposed to cycling loading during their service lives.

BACKGROUND OF THE INVENTION

Structures and machinery components subjected to dynamic loads are prone to experience the formation of cracks and their growth in accordance with the time that the elements are withstanding those loads, also called fatigue loads.

The formation of a crack and its propagation imply a progressive decrease of the strength of the structural element or machinery component which cannot longer work in the intended way for which it was designed and, after a certain time suffering the effect of the fatigue, the residual strength of the structural element is reduced, to the extent that a failure is reached. Hence, it is essential to be able to predict precisely and in real time the decay rate of the residual strength and the remaining life of the structural element.

Fracture mechanics is a branch of science concerned with the study of the propagation of cracks in materials. This field uses methods of analytical solid mechanics to obtain the driving force on a crack and those of experimental solid mechanics to characterize the material resistance to fracture. This field of mechanics helps to predict the service life of structures and machinery components. Applied mechanics covers the analysis of crack tip stress fields as well as the elastic and plastic deformations of the material in the vicinity of the crack. Material science concerns itself with the fracture processes on the scale of atoms and dislocations in the form of impurities and grains.

In order to make a successful use of fracture mechanics in an engineering application, it is essential to have some knowledge of the total technical field.

Fatigue is the weakening of a material caused by repeatedly applied loads. It is the progressive and localized structural damage that occurs when a material is subjected to cyclic loading.

Fatigue failure can occur if the applied load produces an increase in the stress in a point or a zone of the material, with local values exceeding the elastic limit always as a result of the presence of micro-cracks, micro-cavities, local yielding, etc. If the stress is static, the local yielding and the redistribution of the stress onto the surrounding material do not generate any critical condition and the material reaches failure only under considerably higher loads. On the opposite, in the case of dynamic and cyclic loads, the repeated application of the stress leads to the crack propagation until, eventually, the condition of failure is reached and the structural element breaks.

The nominal maximum stress values that cause such damage may be much less than the strength of the material typically quoted as the ultimate stress limit.

Unlike metallic structures and machinery components, historically, concrete structures have not been designed to be subjected to fatigue stresses due to loading cycles along their service lives, which condition their geometry and dimensions. For these scenarios a steel structure was usually chosen or a structure made from another material that was able to resist fatigue.

Generally, concrete was used for structures that, even being able to punctually resist loading cycles, were subjected to other static actions much more determining for their design and dimensioning than fatigue.

Material science has allowed to develop concrete formulas that reach higher strength levels than before and, therefore, civil engineering, in order to extend the application fields of the material, has made possible to use concrete in the design of structures more exigent in terms of fatigue.

Nevertheless, the current codes an international standards, that rule the design of concrete structures, are still vague in relation to the fatigue analysis and do not allow to reach the detail level of assessment necessary to optimize the design of structures subjected to cyclic loads, whose dimensions are conditioned by the concrete fatigue strength.

The standard formulation is limited to derive a concrete fatigue strength from the value of the compressive strength of the material, disregarding many phenomena that significantly influence the concrete fatigue strength. The uncertainties associated to the lack of knowledge about those effects are covered, in the codes and standards, by applying several strong reduction coefficients in order to be always on the safe side.

In the most usual cases, where the structure design and its dimensions are not conditioned by the cyclic loads that will affect the structure along its service life, the standard procedure is considered enough to verify that the structure will not suffer fatigue failure.

Nevertheless, in those special cases where the structure is subjected to cyclic loads in such amount that its design and dimensions are conditioned by the fatigue strength of the concrete, the fact of applying the standard formulation implies the oversizing of the structure and the increase of its cost.

SUMMARY OF THE INVENTION

The purpose of the present invention is to provide a methodology for improving the design of concrete structures subjected and conditioned by cyclic loads along their service lives. To this end the invention consists on a method of design and manufacturing concrete structural elements based on the specification of a concrete fatigue strength value that is later verified as a main control parameter of a quality assurance plan (QAP) carried out during the production stage of the concrete structural elements. The method differs from the standard practice in the total decoupling of the concrete fatigue strength from the compressive strength of the material.

The invention contains a complete procedure to include the control fatigue tests in the quality assurance plan (QAP) of any project. This procedure consists of a sampling and testing plan, a test procedure and the specifications for the testing arrangement, the procedure to analyse the test results, the conformity criteria to validate the concrete structural elements manufactured with the controlled material and the definition of a plan for the non-conformity management.

Furthermore, the invention includes the design of a fatigue machine for simultaneous tests that ensures the performance of the defined methodology and the development of a short duration test procedure that is based on the prediction of the concrete fatigue life according to the secondary strain rate experienced by each test specimen.

Specifically, the present invention proposes a method of design and manufacturing of concrete structural elements involving the following steps:

a) a design phase, including:
  a1) specification of the mechanical characteristics of a concrete, including at least a fatigue strength value as one of the design parameters of a project; and
  a2) definition of the dimensions of concrete structural elements to be manufactured that, in combination with the design parameters specified on step a1) including said fatigue strength value, allow to withstand expected stresses along the service life of said concrete structural elements;
b) a manufacturing and control phase, including:
  b1) manufacturing said concrete structural elements using a concrete and following the element dimensions established on step a2); and
  b2) performing quality controls which includes the extraction of concrete samples during a concrete production phase and the execution of fatigue strength tests over said concrete samples in order to verify that the test results are in accordance with a fatigue strength value that is specified on step a1) of the project.

The concrete used in manufacturing the concrete structural elements is obtained by performing a concrete formulation and producing a concrete according to the mechanical characteristics of the concrete specified on step a1) of the project.

During step a2) the concrete structural elements are dimensioned by calculation, considering the mechanical characteristics of the concrete specified on step a1). This process can provide additional relevant information for the concrete specification, for example related to the structure weight, and therefore it may be necessary to redefine the mechanical characteristics of the concrete, coming back to steps a1) and a2) in order to reach the most suitable result of the design phase.

In the step a1) among several parameters the compressive strength value is also used as a design parameter but the compressive strength value is completely decoupled and independent from said fatigue strength value, in such a way that the value of the fatigue strength is different from a dependent fatigue strength value deducible according a theoretical reduction of the concrete compression strength. Therefore, having a defined compressive strength value, different fatigue strength values can be specified and evaluated during the step a1) of the design phase in order to achieve the most convenient concrete for the calculated structure. Obviously also having a defined fatigue strength value, different compressive strength values can also be evaluated, or both parameters can be modified independently to each other and evaluated.

The specified compressive strength and fatigue strength will be in a rank of technical achievable strength values. According to the present state of the art, the specified compression strength can be comprised between 10 and 200 MPa and the specified fatigue strength can be comprised between 10 and 200 MPa, but these ranks can be increased using further technical improvements in the concrete field without escaping from the scope of protection of the present invention In an embodiment the concrete elements produced on step b1) include reinforcing bars, tendons, pre-tensioned tendons, post-tensioned bars and/or post-tensioned tendons, and these bars and/or tendons are considered on step a2) of definition of the dimensions of said concrete structural elements.

In another embodiment the concrete elements produced on step b1) include reinforcing fibres and these fibres are considered on step a2) of definition of the dimensions of said concrete structural elements. In those cases, the fatigue strength tests are performed over concrete samples and/or concrete test specimens including reinforcing fibres.

The acceptance of all concrete elements produced on step b1) will be evaluated according to the results obtained during the quality controls carried out on step b2) which will include at least compressive strength tests and fatigue strength tests that will be performed over hardened concrete samples manufactured with concrete coming from batches used for manufacturing said concrete structural elements.

From the above it can be summarized that the method proposed consists on decoupling the fatigue strength of the compressive strength, treating the first property as one specified by the project and directly controlled by means of quality controls providing in a quality assurance plan (QAP). Thus the fatigue strength cannot be deduced from the results of the compressive strength tests. Therefore, specific fatigue strength tests have to be performed independently from the compressive strength tests.

According to the invention the implementation of the phase b2) related to performing said quality controls includes, in a preferred embodiment, the following steps:

b21) design of a sampling plan adapted to a production volume and rate of the structural concrete elements, that allows obtaining concrete samples representative of populations, associated to production control lots, whose sizes make possible a suitable characterization of the fatigue phenomenon of the concrete;
  b22) design of a testing plan according to an expected stress history of said structural concrete elements and its critical frequencies, considering the performance of different test series over each sample of specimens in order to characterize the concrete fatigue behaviour for different stress levels;
  b23) obtaining concrete samples following the sampling plan defined on step b21) and the specimens required by the testing plan defined on step b22);
  b24) manufacturing of concrete test specimens with the concrete samples obtained on step b23) according to the testing plan defined on step b22)
  b25) execution of fatigue strength tests over concrete test specimens manufactured on step b24) according to the specifications of the testing plan defined on step b22);
  b26) evaluation of test results obtained on step b25) by the application of statistical procedures that consist on the adjustment of a suitable distribution function and then obtaining characterization parameters in order to determine the design values of the strength associated to an ultimate limit state of fatigue; and
  b27) verification of the acceptance of the structural concrete element manufactured on step b1) by checking that the value of concrete fatigue strength obtained after the evaluation of the test results on step b26) is equal or higher than the fatigue strength value specified in the project on step a1).

Also in a characteristic way of this invention the cited fatigue strength tests of said quality controls of step b2), are performed on a plurality of concrete test specimens in a simultaneous and independent way by at least one fatigue testing machine that produces cyclically, with a controlled frequency, a predefined compression force whose magnitude is controlled and a posterior release of said compression force on said concrete test specimens. In order to implement this, the plurality of concrete test specimens are placed along a longitudinal axis of the fatigue testing machine, being the predefined compression force of controlled magnitude transmitted along said axis and affecting all the concrete test specimens simultaneously. In a preferred embodiment the concrete test specimens are inserted into capsules arranged as a train of capsules located along said longitudinal axis of the fatigue testing machine in such a way that the arrangement of the capsules allows a load transmission along the train.

The strain experienced by each concrete test specimen is registered by sensors during the whole fatigue test in order to relate the strain of each test specimen with the concrete fatigue life of the test specimens.

According to another feature of the invention the duration of fatigue strength tests may be reduced by means of predicting the concrete fatigue life, without actually exhausting all the cycles of said fatigue strength tests, from a relation between the number of resisted cycles N and a secondary strain rate which should be previously obtained from other fatigue strength tests carried out over concrete test specimens manufactured with the same material or similar.

The method proposed in this invention can be applied on the design and manufacturing of concrete structural elements (in situ or precast) that can be used in:
- structures subjected to wind loads, selected among: wind turbines towers and foundations, skyscrapers, large bridges, industrial facilities;
- structures subjected to wave loads selected among: breakwaters and offshore structures including structure foundations, wind tower foundations and platform foundations;
- structures subjected to high cyclic loads due to certain transport systems, selected among: railway bridge decks, railway sub-structures including ballastless track systems and concrete railway sleepers; and
- structures subjected to induced vibrations by industrial machinery selected among: machine foundations and machine supports.

In another preferred embodiment a new concept of wind turbine tower comprising several concrete structural elements, precast or manufactured in situ, connected by their end portions, is provided, wherein the concrete structural elements are produced according to the method of design and manufacturing disclosed and wherein said concrete structural elements work in a fatigue stress range wider than a range established by the standard practice, according to which the fatigue strength value depends simply on the concrete compressive strength.

Due to the application of the new method, this new wind turbine tower is characterized in that the slenderness, which is obtained from the ratio between the tower height and the average thickness of the wall of the structural elements, is greater than the slenderness of the wind turbine concrete towers commercially available nowadays and designed according to the standard practice.

This can be translated to the slenderness of the concrete structural elements that said tower comprises and not necessarily the tower slenderness. Thus, in another embodiment the tower comprises several concrete structural elements characterized in that the slenderness of at least one of them is greater than the slenderness of the concrete rings comprised by the turbine concrete towers commercially available nowadays, being said slenderness obtained from the ratio between the height of the concrete structural element and the average thickness of the wall of said structural element.

Other features of the invention are disclosed in the following detailed description of an exemplary embodiment.

BRIEF DESCRIPTION OF THE DRAWINGS

The invention and its advantages may be more easily understood from the following detailed description when taken in conjunction with the accompanying drawings in which.

DETAILED DESCRIPTION OF THE INVENTION

The design method proposed is based on the verification of the concrete fatigue strength by test as part of the quality assurance plan (QAP) carried out during production.

The design value of the concrete fatigue strength $f_{cd;fat}$ is the parameter that characterizes the fatigue strength of the material. Its value is specified by the project and verified later, but independently of the concrete compressive strength.

The standard practice consists on specifying the characteristic value of the compressive strength $f_{ck}$ as the only strength parameter to control in the quality assurance plan, whilst the rest of the properties that describe the concrete behaviour are derived from the compressive strength. Unlike this standard practice the method proposed in this invention consists on decoupling the fatigue strength of the compressive strength, treating the first property as one specified by the project and directly controlled in the quality assurance plan.

The design value of the concrete fatigue strength $f_{cd;fat}$ should be set related to a series of parameters which represent the actual working conditions of the intended structure and that have not been taken into account in the current standards. These parameters may be:

Reference age for fatigue strength $t_{Ref}$. Age at which fatigue damage starts to be computed in the structure assessment.

Reference relative humidity for fatigue strength $RH_{Ref}$. Minimum relative humidity, specified by project, for which the design value of fatigue strength is defined.

Reference frequency for fatigue strength $f_{Ref}$. Main load frequency specified by project, for which the design value of fatigue strength is defined.

These parameters should also be set during the design of the structure and should appear in the project documentation (drawings, quality assurance documents of production, etc.).

The following sections explain the steps to apply the defined method to the design of concrete structures and the methodology developed to verify the design value of the concrete fatigue strength by tests carried out during the production stage as main part of the quality assessment.

1. Design Application

The assessment of the fatigue damage suffered by the concrete structure is carried out according to a formulation based on the Miner's rule:

$$D = \sum_i D_i = \sum_i \frac{1}{N(\gamma S_k)} \leq 1 \qquad (1)$$

The total damage D is computed as the sum of damages produced by each of the load cycles, i, acting on the section during its lifetime.

According to the expression 1, $N(gS_k)$ represents the design value of the number of resisting cycles $N_d$. The safety factor g to use in the assessment procedure is the product of all three general partial safety factors for loads, materials and consequences of failure, that is:

$$\gamma = \gamma_f \cdot \gamma_m \cdot \gamma_n \qquad (2)$$

Since $f_d = f_k/g_m$ implies $S_d = S_k \cdot \gamma_m$, in terms of design values, the Miner rule may be written as:

$$D = \sum_i D_i = \sum_i \frac{1}{N(S_{cd,i,max}, S_{cd,i,min})} \leq 1 \qquad (3)$$

Where $S_{cd;min}$ and $S_{cd;max}$ are the minimum and maximum stress levels for cycle i, which are defined as:

$$S_{cd,i,max} = \gamma_f \cdot \sigma_{c,i,max}/f_{cd,fat}$$

$$S_{cd,i,min} = \gamma_f \cdot \sigma_{c,i,min}/f_{cd,fat} \qquad (4)$$

With:

$\sigma_{c,i,max}$ is the peak stress for each cycle i.

$\sigma_{c;i;min}$ is the valley stress for each cycle i.

$f_{cd;fat}$ is the design fatigue strength, which implicitly includes $g_m$ and $g_n$ partial safety factors. It is the parameter that characterizes the fatigue strength of the material. Its value is specified in the project the same way as the static compressive strength.

$\gamma_f$ is the safety factor for loads.

$\gamma_m$ is the safety factor for material. In this case, its value is implicitly accounted for through the design fatigue strength.

$\gamma_n$ is the safety factor for consequences of failure. Its value is included in the design fatigue strength value.

Figure 7:
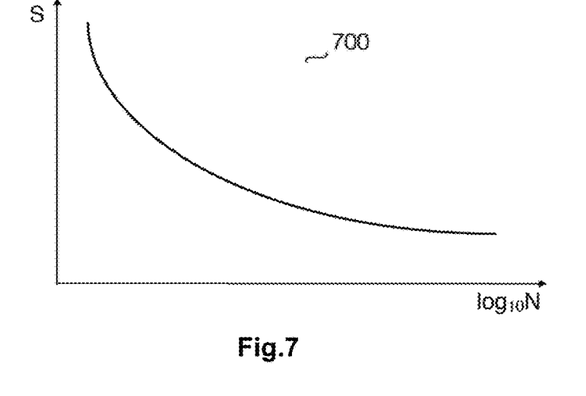
FIG. 7 exemplary shows a diagram with a typical SN curve.

Once defined the stress levels, a curve S–N is obtained in order to relate the fatigue life of the concrete, expressed in terms of resisting cycles N, and the stress levels associated. That curve S–N can be defined according to any proper expression, as the one shown in FIG. 7.

After evaluating the number of resisting cycles for each stress cycle, the damage of each of them corresponds to:

$$D_i = \frac{1}{N} \qquad (5)$$

Finally, all the damages are added to check that:

$$D = \sum_i D_i \leq 1 \qquad (6)$$

If this check is verified, the studied region fulfils ultimate limit state of fatigue.

2. Testing and Quality Assurance 2.1. Terms, Definitions, Symbols and Abbreviations In order to properly develop the experimental procedure to verify the fatigue strength by test and to include this procedure as part of the quality assurance plan of the production, it is necessary to define a series of terms and parameters that will be used throughout the following section as well as the abbreviations and symbols that make reference to them.

2.1.1. General Concepts

Batch

Quantity of fresh concrete which is: mixed in one cycle of operation of a batch mixer, discharged during 1 minute from a continuous mixer or conveyed ready-mixed in a truck mixer when the load requires more than one cycle of a batch mixer or more than one minute of operation of a continuous mixer.

Load

Quantity of concrete transported in a vehicle comprising one or more batches.

Increment

Quantity of concrete taken by the single operation of a scoop or similar sampling device Sample Quantity of concrete taken from a part of a batch or mass of concrete Specimen Concrete piece representative of the material quality. Its shape dimensions and tolerances, manufacturing, curing and conservation are generally standardized. It is used for testing in order to characterize certain material properties. It may be moulded or machined.

2.1.2. Test Parameters

In order to introduce the experimental procedure, it is also necessary to define several parameters:

[m] Number of test configurations.

Total number of different combinations of stress levels that are defined to carry out with tests.

[$C_i$] Test configuration (with i=1 ... m).

Combination of: specimen size and shape, minimum and maximum stress levels, and loading frequency. To facilitate the understanding of the used nomenclature, the numerical sub-indices that accompany the letter C to define a specific test configuration are changed by letters. Thus: $C_i \in \{C_A, C_B, C_C, \ldots, C_m\}$.

[$n_i$] Number of samples tested under configuration $C_i$.

Number of samples tested under the same test configuration $C_i$. Each sample is represented in each test configuration by just one specimen $P_{ij}$. In the end, $n_i$ is the number of specimens tested under each test configuration.

[$S_j$] Sample (with j=1 ... $n_i$).

Concrete volume that is considered as the control production unit of a lot (that is composed by several samples). The material from a sample is used to manufacture a set of specimens. The sample size is defined by the number of specimens that are going to be tested and it corresponds with the number of test configurations, m.

[$P_{ij}$] Specimen (with i=1 ... m and j=1 ... $n_i$).

Single moulded or machined concrete piece coming from a control sample. Each one of the specimens $P_{ij}$ of a test sample $S_j$ will be tested under a different test configuration.

[$L_{m \times n}$] Test lot.

A test lot is a set of samples or test specimens that is considered representative (regarding to their behaviour in fresh state and their mechanical characteristics) of a collection of finished products, a lot, due to they are manufactured under uniform conditions of production with material coming from the same batches.

[$t_{Test}$] Age of each concrete at the time of the test.

Age of each concrete specimen at the beginning of its fatigue test, in days.

[$f_{Test}$] Load frequency for fatigue tests.

Load frequency for fatigue tests (Hz).

[$RH_{Test}$] Relative humidity of concrete at the time of the test.

Relative humidity of storage ambient for concrete samples before fatigue tests, in percentage (%).

2.2. Sampling Plan

The invention implies the definition of a sampling plan which shall be according to the production volume associated to each specific project and the production rate of the factory. This will be specific information for each project according to the production volume required and the particular design of the structure.

The concrete samples for the conformity evaluation should be randomly selected and taken, for example, in accordance with EN 12350-1[1] or ASTM C172 [2].

The sampling frequency must be defined as part of the sampling plan. It could be in accordance with table 17 of clause 8.2, EN 206 [3], at the rate that gives the highest number of samples for initial or continued production, as appropriate, or any other ratios and frequencies that allow performing a correct statistical analysis from the data obtained, as it can be seen in STP 169D [4], sections 3 and 4.

Each sample will be used to manufacture test specimens according to the requirements of the testing plan ( ).

2.3. Testing Plan

The fatigue tests will be performed according to different test configurations $C_i$. For each test configuration a representative set of samples $S_j$ shall be tested.

Figure 8:
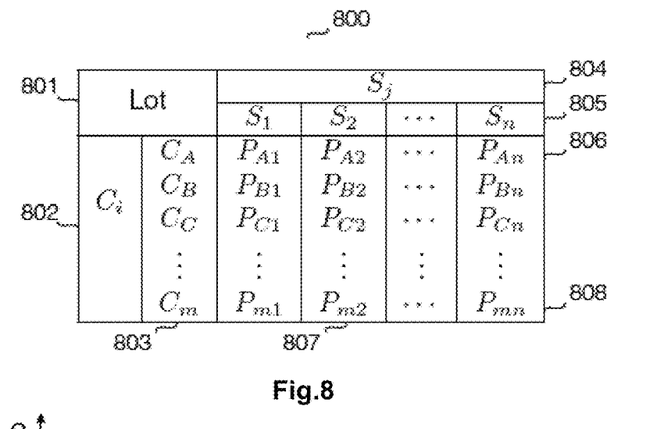
FIG. 8 exemplary illustrates a matrix of test configurations for a possible testing plan in order to complete the explanation of the Quality Assurance Plan based on the evaluation of the concrete fatigue strength given in FIG. 3 following the teachings of this invention.
Figure 9:
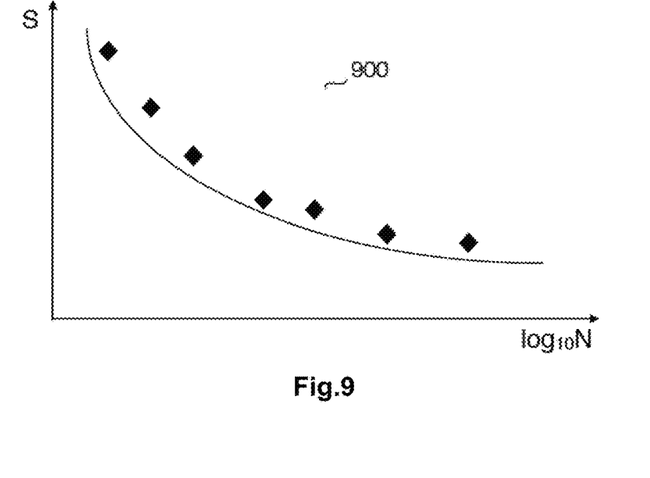
FIG. 9 exemplary shows a graph illustrating the fatigue test results in relation to the $SN_d$ curve, associated to the concrete fatigue strength defined by the project, in order to verify the conformity of a set of concrete specimens regarding to the concrete specification.

A representative set of samples is associated to a control lot. FIG. 8 shows the general conception of all these aspects.

The testing plan should specify the number m of test configurations $C_i$, the number $n_i$ of samples tested under each test configuration $C_i$, the number of specimens per sample and the distribution of the test configurations in the plane S–N in order to ensure a good coverage of both branches of S–N curves.

2.4. Test Specification

This section specifies a procedure to test hardened concrete specimens in order to verify the fatigue strength of the concrete. The stages of the procedure have been defined as an example.

2.4.1. Principle

Test specimens are subjected to load cycles to deal the fatigue failure in a testing machine that may be designed following, as far as possible, the specifications for compressive machines conforming, for example, to EN 12390-4 [5], ASTM C39 [6] or AASHTO T22 [7].

2.4.2. Procedure

The test procedure may imply the following stages:

Selection of stress levels First of all, according to the test configuration that is going to be tested, it is selected a pair of stresses, maximum and minimum of the load cycles, $\sigma_{max}$ and $\sigma_{min}$ (peak and valley respectively), which leads to the number of resisting cycles N established for each test configuration.

The pair of stress values, maximum and minimum, $\sigma_{max}$ and $\sigma_{min}$ drive to a mean value $\sigma_{mean}$. The difference between any of them and the mean value leads to the amplitude of the cycles (in terms of stresses), $\sigma_{amp}$.

$$\sigma_{mean} = \frac{\sigma_{max} + \sigma_{min}}{2} \quad (7)$$

$$\sigma_{amp} = \frac{\sigma_{max} - \sigma_{min}}{2}$$

The loading frequency of the stress cycles $f_{Test}$ is also defined.

Specimen preparation and positioning

It is required to wipe the excess moisture from the surface of the specimen before placing in the testing machine. It is also necessary to wipe all testing machine bearing surfaces, clean and remove any loose grit or other extraneous material from the surfaces of the specimen that will be in contact with the platens.

It should not be used packing, other than auxiliary platens or spacing blocks between the specimen and the platens of the testing machine.

Lastly, before starting the test, it should be ensured that the specimen is positioned in the centre with respect to the one of the platen.

Pre-loading

Once the test specimen is placed, a pre-load should be applied to adjust the platens to the specimen in order to ensure a correct alignment of the load axis.

The pre-load may be between 3.0 to 4.0% of the ultimate compression load of the concrete.

Then, from that stress point, it is applied the mean load defined for the test, according to the test configuration, $P_{mean}$.

$$p_{mean} = \sigma_{mean} \cdot A_{nom} \qquad (8)$$

Loading

The test starts after the pre-loading stage has been carried out. It may be performed in load control. The number of resisting cycles, N is obtained as result of the test and also the strain history experienced by the specimen during the test.

2.5. Testing Arrangement

The requirements for the performance of the testing machine may be the same that those specified in EN 12390-4 [5], ASTM C39 [6] or AASHTO T22 [7], for the performance of the machines used to determine the concrete compressive strength with the following additional requirements:

Capability of executing programmed loading cycles (at different frequencies).

Capability of increasing and reducing the load at constant speed (with a maximum variation of ±0.2 MPa/s).

Capability of keeping a constant load at selectable nominal values (with a maximum variation of ±5%).

Nevertheless, a specific testing machine has been designed to reduce the duration of the experimental campaign of fatigue tests, making easier and cheaper its incorporation to the quality assurance plan that is being performed during the manufacturing process of the structural element.

2.6. Conversion Factors

The methodology developed includes the introduction of a conversion factor $\eta$ in order to take into account the differences between the conditions during the tests and the conditions experimented by the intended structure in its actual environment. All the differences should be accounted by mean of defining several partial conversion factors $\eta_k$.

The conversion factor $\eta$ may be evaluated as the product of the partial factors $\eta_k$ calibrated for each condition or difference involved as:

$$\eta = \Pi \eta_k \qquad (9)$$

A series of partial conversion factors is listed below as an example. Nevertheless, it can be added to that list as many factors as necessary in order to introduce all the corrections required.

[$\eta_s$] Size effect, shape effect and boundary conditions factor.

Fatigue tests are performed over test specimens whose size does not necessarily match the intended structure thickness and whose shape affects the distribution of stresses during the test. Furthermore, while the test is being performed, the specimens are subjected to boundary conditions that may influence the mechanical behaviour of the material. These three phenomena are inherently related and it is not possible to separate them. Thus, an $\eta_s$ coefficient may be calibrated to take into account the influence of those three effect in the concrete fatigue strength.

[$\eta_f$] Loading frequency factor.

Fatigue tests are performed at certain frequencies, while the intended structure works under a continuum spectrum of loads containing all frequencies. It may be necessary to estimate the value of the factor $\eta_f$ to take into account the differences between testing and loading frequencies.

[$\eta_t$] Age Factor.

Due to the inherent large duration of fatigue test, it is inevitable to perform the tests over samples at different ages. Therefore, an age conversion factor $\eta_t$ may be necessary to take into account the differences between reference age (for which $f_{cd;fat}$ is defined) and testing age.

[$\eta_{RH}$] Relative humidity factor.

Fatigue tests are performed over samples that have been stored since the moment of their manufacturing in a determined environment with a specific relative humidity. This condition can significantly modify the fatigue test results. Therefore, the calibration of $\eta_{RH}$ may be necessary in order to take into account the differences between reality and testing humidity conditions.

[$h_w$] Workmanship Factor.

The workmanship conditions, for instance the production according to laboratory conditions instead of actual conditions, may influence structural properties considerably (e.g. properties of joints in assembled structures, fibre orientations in case of using fibre reinforced concrete, etc.). If these effects are considered essential, it may be necessary to estimate the value of the conversion factor $\eta_w$ to take into account the differences between reality and testing conditions.

2.6.1. Calibration Campaign

The calibration of $\eta_k$ factors is carried out independently from the experimental campaign associated to the production quality control of each specific project.

It may be taken into account the reference parameters established by project to define the design value of concrete fatigue strength and those parameters which influence the actual experimental campaign.

The calibration sample size $n_{cs\eta}$ should be big enough to obtain a good representation of the population behaviour under some specific conditions.

The calibration campaign must be composed by as many pairs of calibration series as required to evaluate all the differences between test parameters above mentioned and reference parameters according to the project.

2.7. Evaluation Results

The assessment carried out with the fatigue test results is based on a statistical analysis. The steps of the designed procedure are shown below in order of application.

2.7.1. Evaluation of Stress Levels

The stress levels, $S_{cd;min}(G)$ and $S_{cd;max}(G)$, for each test configuration $C_i$ may be defined as the ratio between valley or peak stress, respectively, and the design value of fatigue strength:

$$S_{cd,min}(C_i) = \frac{\sigma_{c,min}(C_i)}{f_{cd,fat}} \quad (10)$$

$$S_{cd,max}(C_i) = \frac{\sigma_{c,max}(C_i)}{f_{cd,fat}}$$

2.7.2. S N Curve for $S_{cd;min}$

Once defined the stress levels, it may be obtained a curve SN for each minimum stress level $S_{cd;min}$.

2.7.3 Statistical Analysis

The statistical analysis can be carried out according to the distribution function that adjusts in a better way the data obtained from the tests. Then, the analysis is completed by adding different confidence levels and safety factors, according to several coefficients that depend on the method chosen. Two possible methods are described below: the Classical approach and the Bayesian method.

I. Classical Approach

The classical approach is one of the methods proposed by ISO 2394 [8] to deal with the structural design based on experimental models. This method is also documented by ISO 12491 [9] and ISO 16269 [10].

The method allows driving to 95% survival values (lower characteristic values) with a specific confidence level, from the test results, according to the following equation:

$$R_{k,est} = m_R - k_s \cdot s_R \quad (11)$$

Where:
$R_{k;est}$ is the lower characteristic value,
$m_R$ is the sample mean value,
$s_R$ is the sample standard deviation,
$k_s$ is a coefficient based on the non-central Student's t-distribution. It depends on the sample size n, on the probability p corresponding to the desired fractile (related to the survival probability) and on the chosen confidence level.

The resulting characteristic value is later corrected to cover the differences between the testing conditions and the intended structure conditions, by means of the conversion factor η.

Then, the maximum stress level $S_{cd;max}$ associated to each test configuration $C_i$ is further reduced by the safety factor γ, that is obtained as follows.

$$\gamma = \gamma_m \cdot \gamma_n \cdot \gamma_j \quad (12)$$

$$S_{cd,max}(C_i)_\gamma = \frac{S_{cd,max}(C_i)}{\gamma} \quad (13)$$

This leads therefore to a point in the plane $\log_{10}N-S_{cd;max}$ that must be over the previously calculated $SN_i$ curve.

II. Bayesian Method

The Bayesian method is another method proposed by ISO 2394 [8] to deal with the structural design based on experimental models, specifically if a direct evaluation of the test results is desired. This method is also documented by ISO 12491 [9].

The method allows estimating directly the design value from test data according to the following equation:

$$R_d = m_R - t_{vd} \cdot s_R \cdot \sqrt{1 + \frac{1}{n_i}} \quad (14)$$

Where:
$R_d$ is the design value of test results,
$m_R$ is the sample mean value,
$s_R$ is the sample standard deviation,
$n_i$ is the number of tests performed under the same test configuration
$t_{vd}$ is the coefficient of the Student's distribution. It depends on the considered number of freedom degrees (ν=ni−1) and on the $\beta_R$ coefficient. $\beta_R = \alpha_d \cdot \beta$ where β is the target reliability index and ad is the design value for First Order Reliability Method (FORM) influence coefficient.

The resulting design value is later corrected to cover the differences between the testing conditions and the intended structure conditions, by means of the conversion factor η.

This leads therefore to a point in the plane $\log_{10}N-S_{cd;max}$ that must be over the previously calculated $SN_i$ curve.

2.8. Conformity Criteria

For each configuration test $C_i$ the design value of the logarithm of the number of resisted cycles is assessed according to a statistical procedure. In the example exposed this analysis is based on two different methods:
Direct evaluation by classical approach,
Direct evaluation by Bayesian method.

The lot will be accepted if the values obtained applying the statistical analysis are on the safe side, over the calculated $SN_d$ curve obtained from the specified value of fatigue strength $f_{cd;fat}$.

2.9. Non-Conformity Management

In case of non-conformity, it is necessary to take into account a procedure to manage the lot affected. The following actions may be part of the aforementioned procedure, to be taken in the event of non-conformity:

Check test results and if the evaluation has been wrong, take actions to eliminate and correct mistakes.

Verify if there is actually some test configuration with non-conformities or if all of them are out of conformity. If the non-conformity is related to the results of just one test configuration, repeat the test (same configuration) over additional samples, which were manufactured with the same material and therefore are representative of the same lot.

If non-conformity is confirmed or if there are more than one test configuration out of conformity, the following corrective actions could be taken in the order of appearance, including a management review of relevant production control procedures:

Inform to the specifier(s) and user(s) in order to avoid any consequential damage.

Check test machines and calibrate them again with patron samples monitored in order to be sure that the mistake is due to the concrete and not to the test equipment.

Check tolerances in local standards to control the rejection of units.

Check and repeat the structure assessment in order to verify the correct behaviour of the structure even with a reduced fatigue strength (obtained from tests) with regard to the specified value.

Check the loads used for the design in collaboration with the structure designer.

Evaluate the possible options to strengthen the structure or repair it.

Demolish/replace the units that are not in conformity with the requirement for new pieces.

Record actions on the items above.

If the results of conformity test do not fulfil the requirements, before demolishing or replacing the pieces, supplementary testing can be performed on cores taken from the structure or components. Also a combination of tests on cores and non-destructive tests on the structure or components may be carried out.

3. Accelerated Testing Procedure

Due to the inherent large duration of fatigue test and the high cost that implies the execution of the required number of fatigue tests for a suitable statistical analysis of the results, the proper application of the invention could be difficult or even impossible for many projects. In order to facilitate the application of the defined method and its inclusion in the quality assurance plan associated to the production stage of each project, two strategies have been developed:

The first of them consists on the execution of the fatigue test simultaneously over several concrete specimens in order to increase the rate of attainment of results. This could be carried out using several testing machines or, what is a product of the invention, using just one fatigue testing machine that allows testing several specimens simultaneously.

The second proposed strategy refers to a test procedure of short duration based on the strain history of each specimen along the test.

These strategies may be applied independently of each other or together, according to the schedule constraints. Both of them are detailed below.

3.1. Fatigue Testing Machine

Figure 4:
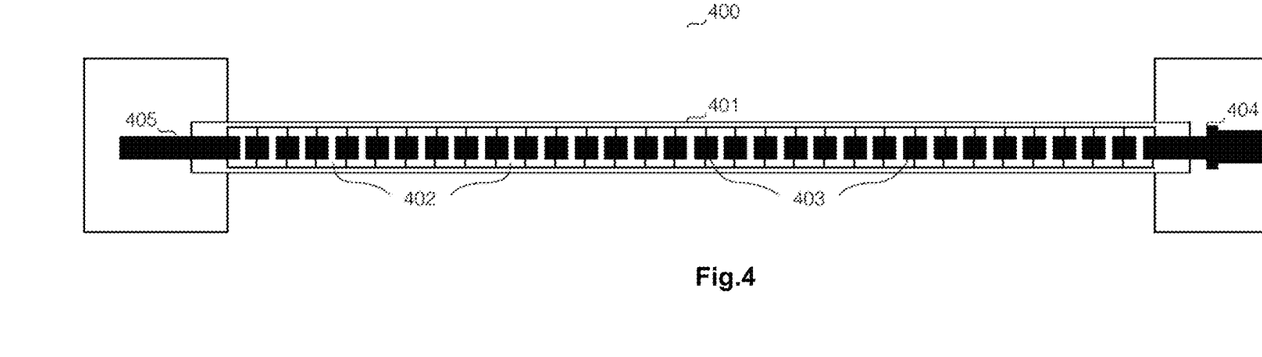
FIG. 4 shows a schematic top view of an example of fatigue testing machine for testing simultaneously 30 specimens.

As it has been said before, the strategy to speed up the obtention of data is based on the performance of several fatigue test simultaneously. The optimum way to carry out this plan consists on using a testing machine that allows performing many fatigue tests at the same time. An example of this machine is shown in FIG. 4.

The testing machine designed is based on the definition of a train of test specimens. The longitudinal axis has a drive cylinder at one end and a reaction cap at the other.

The main characteristic of the fatigue machine is that it allows testing several specimens simultaneously until all of them reach the breaking point. This is possible due to the design of the capsules, where the test specimens are placed, allows the loading transmission in a correct way along the train, independently of the state of the samples.

The designed machine allows to determine the maximum and minimum loads and stresses of the loading cycles as well as to measure the strain experienced by each of the specimens during the test. This is carried out by mean of two measuring systems in order to compare the obtained data and make the needed corrections.

3.2. Test Procedure of Short Duration

The second proposed strategy, in order to speed up the attainment of data from fatigue tests, is based on the definition of a test procedure of short duration that consists on the extrapolation of the fatigue life according to the strain history of each concrete specimen.

The concrete specimens suffer deformations during fatigue tests that can be registered. The strain gradually increases with increasing the number of stress cycles. If the deformation is plotted as a function of the number of resisting cycles, the resulting curve is similar to the one shown in FIG. 5.

Figure 5:
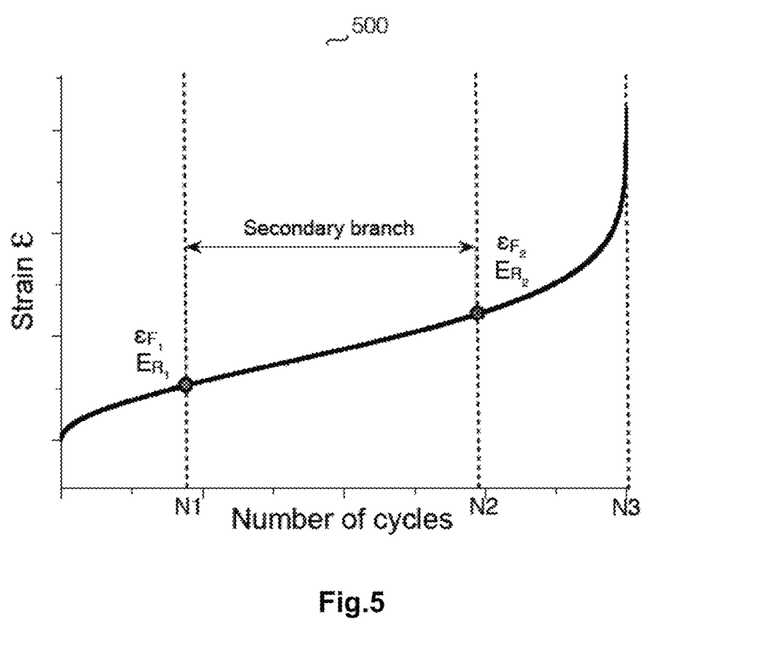
FIG. 5 shows an explanatory diagram illustrating a typical curve for the evolution of strain with respect to cycles in a fatigue test, where it can be appreciated the behaviour trend of the concrete in terms of strain along the test and see the different branches of the curve, being the second branch and its slope the most significant for the evaluation of the fatigue test results.

The curve $\varepsilon$–N is analysed by dividing it in 3 branches related to the different stages of the strain development. Generally, this curve presents a rapid increase at the beginning, from 0 until it is reached the 10% of total life, a uniform increase from 10 to approximately 80% (secondary branch) and then a rapid increase until failure.

It is especially important for this procedure the strain development in the secondary branch on which the increase of strain $\varepsilon$ is constant. The slope of this branch is called secondary strain rate, $\dot{\varepsilon}$.

Figure 6:
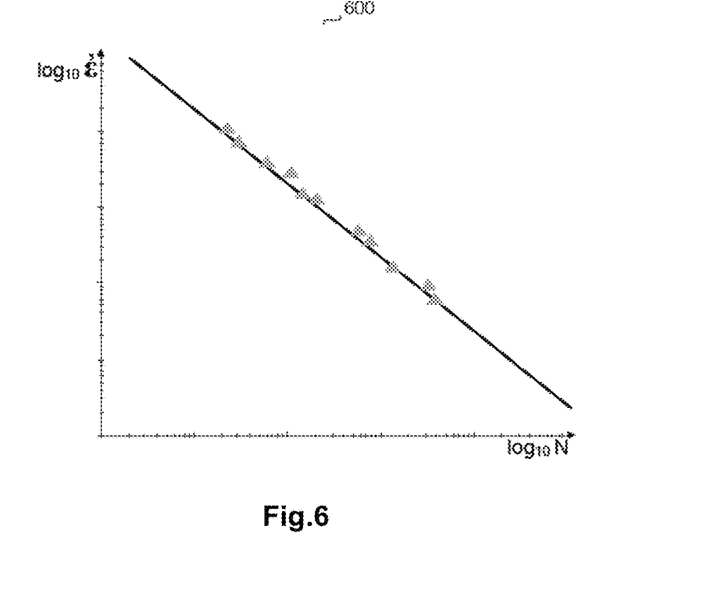
FIG. 6 exemplary shows an explanatory diagram illustrating the relation between the secondary strain rate experienced by several concrete specimens along their fatigue tests and the number of cycles resisted by each one of them.

There is a strong relation between the secondary strain rate $\dot{\varepsilon}$ and the number of cycles to failure N or fatigue life, as it is shown in FIG. 6.

The test procedure of short duration consists on the prediction of the number of resisting cycles to failure or, what is the same, the fatigue life of the specimen, from the relation between N and which is previously obtained from other fatigue tests carried out over concrete specimens manufactured with the same material. The prediction may be carried out at the beginning of the secondary branch without actually exhausting all the cycles, what means that the time spent on the test execution is reduced.

The fact of carrying out the tests with the fatigue machine defined before, which is able to perform several test simultaneously, and following the test procedure of short duration explained in this section, allows to reduce the duration of the experimental campaign up to several hundreds of times in comparison with the application of the standard procedure.

4. Comparison Between the New Method and the Standard Practice

Figure 1:
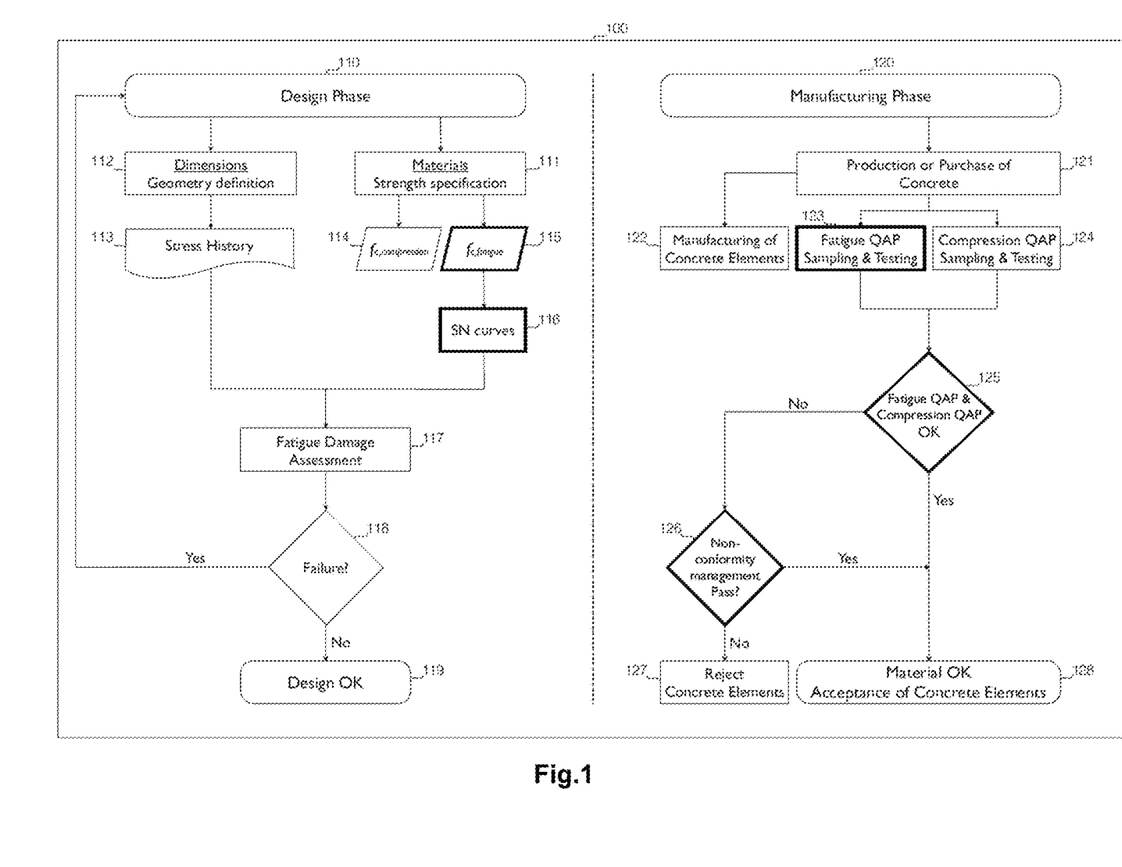
FIG. 1 shows two flow charts illustrating in conjunction an embodiment of the proposed invention including the assessment of the fatigue damage in the design phase and the verification of the product acceptance during the manufacturing phase comprising a Quality Assurance Plan (QAP) based on the fatigue behaviour of the concrete, besides the traditional control based on the concrete compressive strength.
Figure 2:
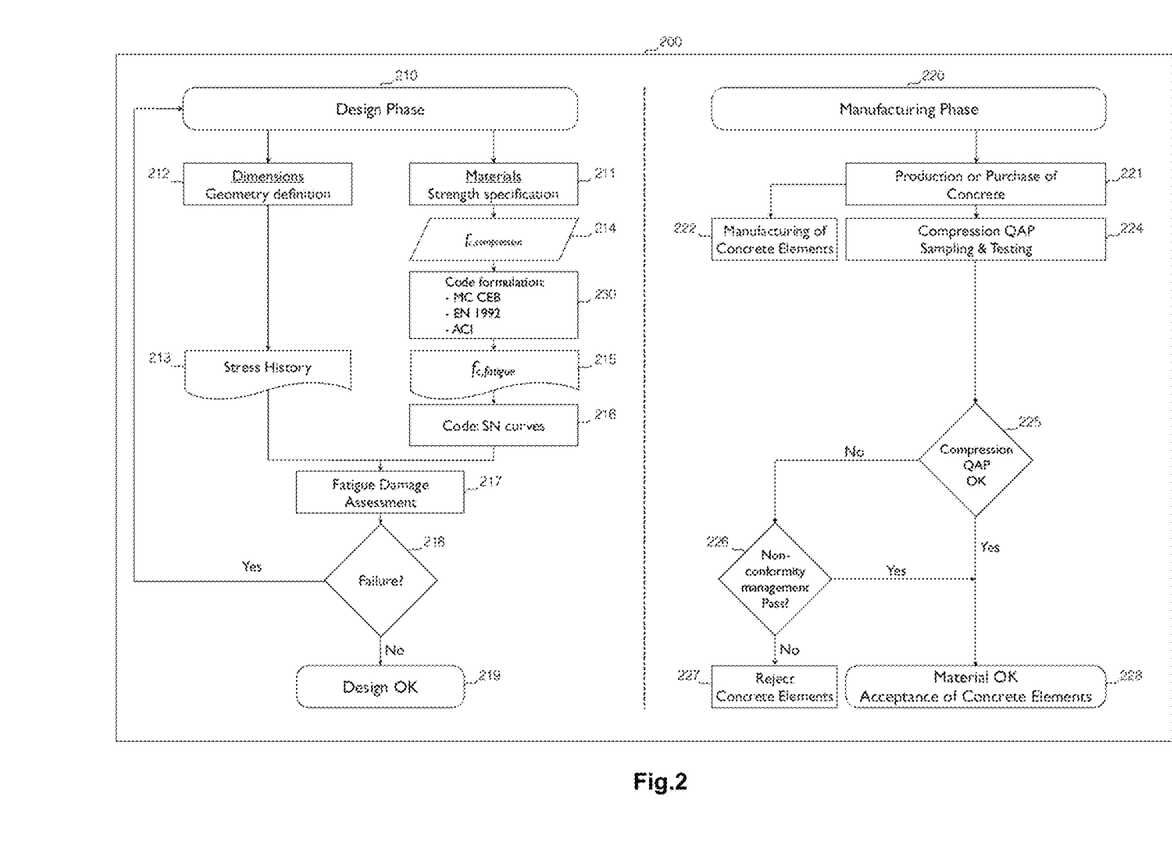
FIG. 2 shows two flow charts illustrating in conjunction an embodiment of the traditional procedure of assessing the structure fatigue damage in the design phase and the verification of the product acceptance during the manufacturing phase as result of the Quality Assurance Plan that is based on the evaluation of the concrete compressive strength.

In order to highlight the differences between the proposed method 100 and the standard method 200, FIG. 1 shows a flowchart of the proposed method 100, including a design phase 110, and a manufacturing phase 120, and FIG. 2 shows a flowchart of the standard method 200, according to the state of the art, including a standard design phase 210 and a standard manufacturing phase 220.

As per the state of the art, shown in FIG. 2, the standard design phase 210 comprises the specification of the mechanical characteristics of a concrete 211 including a compressive strength value 214 as a main design parameter. The fatigue strength value 215 is derived from said compressive strength value 214 by applying a formulation established and approved by an international code or standard 230 in such a way that the fatigue strength value 215 is completely dependent on the compressive strength value 214 specified by the project 211. Once defined the stress levels and depending on said fatigue strength value 215, a stress-cycles curve 216, thereafter called S-N curve, is obtained in order to relate the fatigue life of the concrete, expressed in terms of resisting cycles N, and the stress levels associated. That curve 216 is defined according to the expression proposed by the code or standard that rules the project.

The standard design phase 210 of the standard method 200 also includes the definition of dimensions 212 of concrete structural elements.

Once said fatigue strength value 215 is obtained, and after the definition of dimensions of the concrete structural element, in combination with a stress history 213 of similar structures, a fatigue damage assessment 217 can be performed. If the result of said assessment is the forecast of a structural failure, the design phase 210 has to be adjusted, if not the standard design phase 210 is considered completed 219.

The standard manufacturing phase 220 includes the formulation and production of a concrete 221 according to the mechanical characteristics 211 specified on the standard design phase 210. The designed concrete structural elements 222 are produced by using said concrete formulated and produced 221 and also concrete samples are obtained for carrying out the quality control 224 which is based mainly on compressive strength tests of specimens manufactured with said produced concrete 221, which generally constitute the quality control test assessing the fulfilling of the specified mechanical characteristics of the concrete 211, producing the acceptance 228 of the manufactured concrete structural elements 222, or the rejection 227 of said manufacture concrete structural elements 222. The description above corresponds to the standard method 200.

As opposed to the above, FIG. 1 shows the proposed method 100, in which the design phase 110 includes the specification of the mechanical characteristics of a concrete 121, including as one of the design parameters of a project 111 the compressive strength 114 as well as the fatigue strength 115 of the concrete but being both parameters independent and not related to each other, and therefore being independently specified. This is the first main difference between the standard method of design of concrete structural elements 200 and the proposed method 100.

Once defined the stress levels, and depending on said specified fatigue strength 115 a stress-cycles curve, thereafter called $S_N$ curve 116, is obtained (see FIG. 7 as an example) in order to relate the fatigue life of the concrete, expressed in terms of resisting cycles N, and the stress levels associated. That curve 700 can be defined according to any proper expression.

The definition of dimensions 112 of the concrete structural element is also carried out as part of said design phase 110.

A fatigue damage assessment 117 is performed combining the specified mechanical characteristics of the concrete 121, the S–N curve 116, the dimensions 112 of the concrete structural element and also a stress history 113 obtained from similar structures in the past. As result of said fatigue damage assessment 117, a structure failure 118 can be forecast, forcing to modify the design parameters determined in the design phase 110 or the design to overcome the evaluation producing the acceptance of the design 119.

The proposed manufacturing phase 120 includes the formulation and production of a concrete 121 that may be according to the mechanical characteristics of the concrete specified on the standard design phase 110. This produced concrete 121 is used in the manufacturing of the concrete structural elements 122, and also in obtaining concrete samples used in the fatigue quality controls 123 and in the compression quality controls 124 too. A plurality of specimens is obtained from said concrete samples and compressive strength tests and fatigue strength tests 328 are performed on said specimens 327 in order to determine if said produced concrete 121 would fulfil the specification of the proposed design phase 110 producing the acceptance 128 of the manufactured concrete structural elements 122 or not, producing the rejection 127 of said manufactured concrete structural elements 122.

The quality control, focused on the evaluation of concrete fatigue strength 123 and also of compressive strength 124, constitutes an essential difference between the standard method shown in FIG. 2 and the proposed method shown in FIG. 1, which includes fatigue strength tests 328 in the quality control procedure. This is necessary because in the proposed method 100 the specified compressive strength 114 and the specified fatigue strength 115 are not related to each other, and therefore the result of the compressive strength test does not provide information about the fatigue strength of the manufactured concrete structural elements 122, being necessary the performance of the cited fatigue strength tests 328.

Figure 3:
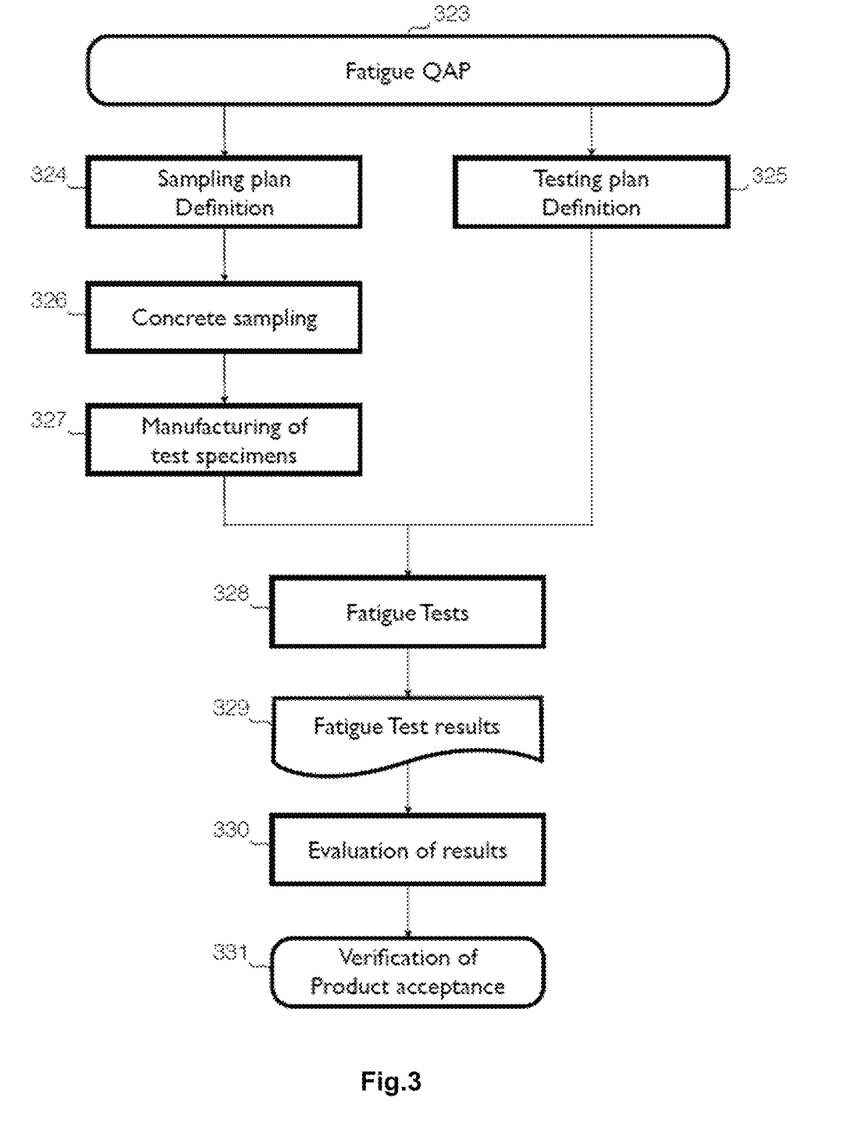
FIG. 3 shows a flow chart of the proposed quality control procedure illustrating an example of a Quality Assurance Plan, based on the evaluation of the concrete fatigue strength, and the steps involved in the process to be followed.

A detailed description of the steps proposed to perform the above described fatigue quality assurance plan (QAP) is shown on FIG. 3.

The fatigue quality assurance plan (QAP) includes the design of a sampling plan 324 and a testing plan 325 according to the production requirements and concrete service life provisions, which provides information allowing the characterization of the fatigue phenomenon associated to the entire concrete population.

Once the sampling plan 324 has been defined, concrete samples 326 are obtained from the concrete produced during the concrete production 121, and test specimens 327 are manufactured from said concrete samples 326.

The number of concrete samples 326 will be defined by the sampling plan 324, and the number of test specimens 327 produced from each concrete sample 326 will be defined by the number of different test to be performed on each concrete sample 326, defined on the testing plan 325, thus each concrete sample 326 will be submitted to different testing conditions, for example different frequencies or stress levels, and a single specimen 327 from a concrete sample will be necessary for each test condition.

The test specimens 327 will be then submitted to fatigue tests 328, and the results 329 will be then evaluated 330 in order to verify the product acceptance 331.

The fatigue tests 328 are time-consuming because each test specimen 327 has to be submitted to thousands of compression cycles in order to determine the weakening of the specimen 327 along the fatigue test 328, and a big amount of specimens 327 have to be tested to determine the fatigue strength of each concrete sample 326 in said different testing conditions.

To achieve a time cost reduction of said fatigue tests 328, a special fatigue testing machine 400 has been developed, allowing a simultaneous and independent testing of a plurality of test specimens 327 using a single testing machine 400, schematically shown on FIG. 4.

On said testing machine 400 a plurality of concrete test specimens 327 are placed along an axis of the fatigue testing machine 400 conforming a test train 401 placed between a drive cylinder 404 and a reaction cap 405, and inserted into capsules 402. Said capsules 402 allow the transmission of a compression force through the test specimens 327.

The displacement of the drive cylinder in the axis direction with a controlled velocity, acceleration and force will produce the simultaneous compression of all the test specimens 327, allowing the simultaneous testing of a plurality of test specimens with a single machine 400.

Each test specimen 327 will be independently monitored by sensors, detecting the strain experienced by each single test specimen 327.

Preferably said capsules 402 will be able to transmit the compression forces through the test specimens 327 while said test specimens 327 withstand the cyclic compressive forces. Obviously not all the test specimens 327 simultaneously tested in the fatigue testing machine 400 will reach the failure at the same time due to the concrete heterogeneity. Said capsules 402 will retain any fragment of the collapsed test specimens 327 and will transmit the compressive force instead of the collapse test specimen 327, from the previous to the subsequent test specimen 327. This feature will allow the proposed testing machine 400 to continue with the fatigue test 328 until all of the concrete test specimen 327 reach the failure even if some of them collapse before that the others.

The following sections introduce, by mean of several examples, the relationship between the design method that has been developed based on the improved fatigue strength obtained by test, and the general design procedure (standard practice).

4.1. Comparison in Terms of Technical Design Parameters

The first level of comparison is related to the technical design parameters that have been conventionally used to determine the concrete fatigue strength.

The developed method allows to take into account many aspects as the relative humidity of the ambient, the loading frequencies or the age of the concrete between others that are disregarded by the current standards. All this drive to the obtention of a realistic value of the concrete fatigue strength for each specific case that redounds in higher admissible stresses for the material.

On one side, the maximum stress resisted by a specific material for a given number of cycles is going to be analyzed according to the standard practice and using the developed method (fatigue verification by tests).

On the other side, the analysis will be focused on the quality of the concrete (in terms of characteristic compressive strength) that is required according to each methodology to resist the same number of stress cycles for the same value of maximum stress associated.

4.1.1. Maximum Allowable Stresses

The material that is going to be analysed is a concrete with a characteristic compressive strength of 70 MPa (C70) that reaches the fatigue failure at $10^6$ stress cycles.

After performing the relevant calculations, that are not included here in order to simplify the text, the conclusion related to the maximum stress $\sigma_{c,max}$ resisted by a structure 1 million times ($10^6$ cycles) and made of this C70 concrete is:

According to the formulation of Model Code (1990) [11]:
$\sigma_{c,max}$=12.98 MPa, that means 19% of $f_{ck}$
According to the formulation of EuroCode 2, [12] and [13]:
$\sigma_{c,max}$=13.84 MPa, that means 20% of $f_{ck}$
According to the design method developed:
$\sigma_{c,max}$=22.61 MPa, that means 32% of $f_{ck}$ This example has been developed for a conventional concrete of 70 MPa of characteristic compressive strength but it could be analysed for any other strength values too.

According to the developed methodology, the concrete structures may work subjected to higher fatigue stresses than those that supposedly withstands as per current regulations, always being on the safe side.

4.1.2. Concrete Quality Grades

As aforementioned, another way to see the differences between both methodologies is to compare the concrete quality grade required for the structure, in terms of characteristic compressive strength, to resist N cycles under $\sigma_{c,max}$ following the standard practice and according to the new methodology.

Thus, if the considered maximum stress $\sigma_{c,max}$=13.0 MPa, and the associated value of resisted cycles N=$10^6$ cycles, then:
According to the Model Code (1990) [11], it would be needed a concrete with: $f_{ck}$=70 MPa.
According to the EuroCode 2 [12] and [13], it would be needed a concrete with: $f_{ck}$=65 MPa.
According to the design method it would be needed a concrete with: $f_{ck}$=40 MPa.

4.2. Comparison in Terms of Resultant Structural Typology

The method described above has its main application in the design of concrete structures subjected to cycling loading during their service lives. Likewise a new concept of wind turbine tower derives from its application.

Thus, the second level of comparison is related to the results that can be obtained by applying this new method in the design of concrete structures rather than the general procedure established by the current codes and standards (IEC 61400 [14] and Model Code 1990 [11]) and furthermore the new concept of wind turbine tower derived from its application.

The accurate determination of the concrete fatigue strength is mainly reflected in parameters of the structure geometry. So, for the example of a wind turbine tower, the geometrical parameters affected would be the wall thickness and, therefore, the concrete volume.

The example is particularized for a pre-stressed concrete tower that is 100 m tall and comprises 5 rings that are 20 m tall each one. The intended wind turbine is a 2.0 MW wind turbine.

If the analysis is conducted in terms of concrete quality grades, considering a wall thickness of 16.0 cm and a total concrete volume per tower of 300 m3, applying the new method a characteristic compressive strength of 45 MPa would be required instead of an 80 MPa concrete, as required by the current regulations.

If the analysis is conducted in terms of geometrical parameters, considering a C80 concrete ($f_{ck}$=80 MPa), the minimum wall thickness required by the tower shell may be 10.0 cm if the accurate fatigue strength obtained by means of the developed methodology is applied; whereas if the standard practice is followed, the required thickness is, at least, 16.0 cm.

In terms of concrete volume, it could be said that with the application of the new method, the pre-stressed tower would require 190 m3 of concrete and, according to the general formulation, the required concrete volume would be 300 m3. This implies a reduction of, at least, 35% in the cost of concrete production and in tower weight, as well as a reduction in transport costs.

The new tower concept mentioned above considers another possibility. If instead of reducing the concrete volume this is kept constant (300 m3) and the wall thickness is reduced according to a C80 concrete (10.0 cm), which the new method allows, it is possible to assume a significant increase in the tower height, using the same crane typology. Thus, in this example, the tower height would result in 135 m (instead of 100 m) and the tower slenderness, obtained from the ratio between the tower height and the wall thickness required by the tower shell, would be 1350, whereas if the standard practice is followed and the same tower height is considered (which could not be possible with that concrete quality grade), the slenderness would be 844.

It is to be noted that nowadays the height of tower sectors is limited, in most of the cases, because of the capacity of the cranes, which are not usually able to lift the weight associated to those large pieces to the necessary height.

So, this new tower will consist of rings that could be, at least, a 35% higher than those that are designed and calculated according to the standard practice, but they will be lifted by using commercially available cranes. The result will be a new tower generation, which will be able to reach higher heights.

If the example is particularized for the tower described above in terms of the number of concrete sectors required by the structure to reach 100 m height, according to the new method could be possible to reduce from 5 to 3 rings and increase the slenderness of the concrete structural elements (or rings) from 125 (from the ratio between 20 m length and a thickness of 16 cm) to 333 (from the ratio between 33 m length and a thickness of 10 cm).

REFERENCES

[1] CEN (2009). EN 12350-1, Testing fresh concrete—Part 1: Sampling. European Committee for Standardization, 2009. 19
[2] ASTM (2014). ASTM C172/C172M-14a, Standard Practice for Sampling Freshly Mixed Concrete. American Society of the International Association of Testing and Materials, 2014. 19
[3] CEN (2013). EN 206, Concrete. Specification, performance, production and conformity. European Committee for Standardization, 2013. 19
[4] Joseph F. Lamond and James H. Pielert. Significance of tests and properties of concrete and concrete-making materials. American Society of the International Association of Testing and Materials, 2006. 19
[5] CEN (2001). EN 12390-4, Testing hardened concrete—Part 4: Compressive strength—Specification for testing machines. European Committee for Standardization, 2001. 20, 22
[6] ASTM (2015). ASTM C39/C39M-15a, Standard Test Method for Compressive Strength of Cylindrical Concrete Specimens. American Society of the International Association of Testing and Materials, 2015. 20, 22
[7] AASHTO (2014). AASHTO T22-14, Standard Method of Test for Compressive Strength of Cylindrical Concrete Specimens. American Association of State Highway and Transportation Officials, 2014. 20, 22
[8] ISO (1998). ISO 2394:1998 General principles on reliability for structures. International Organization for Standardization, 1998. 26, 27
[9] ISO (1997). ISO 12491:1997 Statistical methods for quality control of building materials and components. International Organization for Standardization, 1997. 26, 27
[10] ISO (2014). ISO 16269: Statistical interpretation of data. International Organization for Standardization, 2014. 26
[11] CEB-FIP (1990). CEB-FIP Model Code 1990, Design Code. Final Draft. Comite Euro-International du Beton, Bulletins d'Information Nos. 203-205, 1991. 39, 40
[12] CEN (2004). EN 1992-1-1, Eurocode 2: Design of concrete structures—Part 1-1: General rules and rules for buildings. European Committee for Standardization, 2004. 39, 40
[13] CEN (2005). EN 1992-2, Eurocode 2: Design of concrete structures—Part 2: Concrete bridges—Design and detailing rules. European Committee for Standardization, 2005. 39, 40
[14] IEC (2008). IEC 61400-1 Wind turbines—Part 1: Design requirements. International Electrotechnical Commission, 2008. 40

The invention claimed is:
1. A method of designing and manufacturing concrete structural elements comprising:
   a) a design phase wherein design parameters of a project are defined, the design phase including:
      a1) specifying mechanical characteristics of a concrete, including at least a fatigue strength value as one of the design parameters of the project; and
      a2) defining dimensions of the concrete structural elements to be manufactured using the design parameters specified on step a1) including said fatigue strength value, said dimensions being defined to withstand expected stresses along the service life of said concrete structural elements;
   b) a manufacturing and control phase, including:
      b1) manufacturing said concrete structural elements using said concrete and following the dimensions of the concrete structural elements defined on step a2); and
      b2) performing quality controls which includes the extraction of concrete samples during a concrete production phase and the execution of fatigue strength tests over said concrete samples obtaining test results, in order to verify that the test results are in accordance with said fatigue strength value that is specified on step a1) of the project.

2. Method according to claim 1, wherein said concrete used in manufacturing the concrete structural elements is obtained by performing a concrete formulation and producing the concrete according to the mechanical characteristics of the concrete specified on step a1) of the project.

3. Method according to claim 1, wherein said mechanical characteristics of the concrete specified on step a1) of the project further including a compressive strength value as one of the design parameters completely decoupled from said fatigue strength value, being both the compressive strength value and the fatigue strength value design parameters specified by the project and independent of each other.

4. Method according to claim 1, wherein said phase b2) includes the following steps:
   b21) designing a sampling plan to obtain said concrete samples, said sampling plan being adapted to a production volume and rate of said structural concrete elements, and said concrete samples being associated to production control lots, and being representative of populations which sizes permits a characterization of fatigue phenomenon of the concrete;
   b22) designing a testing plan to perform different test series using different stress levels over different specimens of each of said concrete samples according to an expected stress history of said structural concrete elements and its critical frequencies, considering the performance of the different test series over said different specimens of each concrete sample in order to characterize a concrete fatigue behaviour for said different stress levels;
   b23) obtaining concrete samples following the sampling plan defined on step b21), and obtaining from each of said concrete samples the specimens to be tested according to the testing plan defined on step b22);

b24) manufacturing concrete test specimens with the concrete samples obtained on step b23) according to the testing plan defined on step b22)

b25) executing the fatigue strength tests over the concrete test specimens manufactured on step b24) according to the specifications of the testing plan defined on step b22);

b26) evaluating test results obtained on step b25) by the application of statistical procedures that consist of the adjustment of a distribution function and then obtaining characterization parameters in order to determine fatigue strength design values associated to an ultimate limit state of fatigue;

b27) verifying an acceptance of the concrete structural element manufactured on step b1) by checking that the fatigue strength design values obtained after the evaluation of the test results on step b26) is equal to or higher than the fatigue strength value specified by the project on step a1).

5. Method according claim 4 wherein a strain experienced by each concrete test specimen is registered by sensors during the whole fatigue strength test in order to relate the strain of each test specimen with a concrete fatigue life of said test specimen.

6. Method according to claim 5 wherein during the fatigue strength tests multiple load cycles are performed, and wherein the duration of fatigue strength tests is reduced by means of predicting the concrete fatigue life, without actually exhausting all the load cycles of said fatigue strength tests, from a relation between a number of resisted load cycles N and a secondary strain rate which was previously obtained from other fatigue strength tests carried out over concrete test specimens manufactured with the same material.

7. Method according to claim 1 wherein said fatigue strength tests, of said quality controls of step b2), are performed on a plurality of concrete test specimens in a simultaneous and independent way by at least one fatigue testing machine.

8. Method according to claim 7 wherein said at least one fatigue testing machine produces cyclically, with a controlled frequency, a predefined compression force whose magnitude is controlled and a posterior release of said compression force on said plurality of concrete test specimens.

9. Method according to claim 8 wherein the plurality of concrete test specimens are placed along a longitudinal axis of said fatigue testing machine, wherein the predefined compression force of controlled magnitude is transmitted along said axis and affecting all of the plurality of concrete test specimens simultaneously.

10. Method according to claim 9 wherein said plurality of concrete test specimens are inserted into capsules arranged as a train of capsules located along said longitudinal axis of the fatigue testing machine in such a way that said arrangement of the capsules allows a load transmission along the train.

11. Method according to claim 1 wherein the concrete elements produced on step b1) include reinforcing bars, tendons, pre-tensioned bars, pre-tensioned tendons, post-tensioned bars and/or post-tensioned tendons, and wherein during step a2) of defining the dimensions of said concrete structural elements the dimensions of the concrete structural elements are defined also considering said bars and/or tendons included in the concrete structural elements.

12. Method according to claim 1 wherein said concrete elements produced on step b1) include reinforcing fibers, and wherein during step a2) of defining the dimensions of said concrete structural elements the dimensions of the concrete structural elements are defined also considering said fibers included in the concrete structural elements, and wherein the fatigue strength tests are performed over the concrete samples and/or the concrete test specimens including said reinforcing fibers.

13. Method according to claim 1 wherein the concrete structural elements, precast or manufactured in situ, are used in:
   structures subjected to wind loads, selected among: wind turbines towers and foundations, skyscrapers, bridges, industrial facilities;
   structures subjected to wave loads selected among: breakwaters and offshore structures including structure foundations, wind tower foundations and platform foundations;
   structures subjected to high cyclic loads due to certain transport systems, selected among: railway bridge decks, railway sub-structures including ballastless track systems and concrete railway sleepers; and
   structures subjected to induced vibrations by industrial machinery selected among: machine foundations and machine supports.

* * * * *